US007448258B2

(12) United States Patent
Saunders et al.

(10) Patent No.: US 7,448,258 B2
(45) Date of Patent: Nov. 11, 2008

(54) HIGH THROUGHPUT SCREENING FOR MOISTURE BARRIER CHARACTERISTICS OF MATERIALS

(75) Inventors: Dennis L. Saunders, San Dimas, CA (US); Radislav A. Potyrailo, Niskayuna, NY (US)

(73) Assignee: Avery Dennison Corporation, Pasadena, CA (US)

(*) Notice: Subject to any disclaimer, the term of this patent is extended or adjusted under 35 U.S.C. 154(b) by 1651 days.

(21) Appl. No.: 09/860,197

(22) Filed: May 17, 2001

(65) Prior Publication Data

US 2001/0034063 A1 Oct. 25, 2001

Related U.S. Application Data

(63) Continuation-in-part of application No. PCT/US00/29854, filed on Oct. 30, 2000, and a continuation-in-part of application No. PCT/US00/29990, filed on Oct. 30, 2000.

(60) Provisional application No. 60/162,349, filed on Oct. 29, 1999.

(51) Int. Cl.
*G01N 5/02* (2006.01)
(52) U.S. Cl. ............... 73/73; 427/8; 356/402; 356/437
(58) Field of Classification Search ............ 427/8; 73/73; 356/402, 432, 436, 437
See application file for complete search history.

(56) References Cited

U.S. PATENT DOCUMENTS

| 4,013,806 | A |   | 3/1977  | Volkert et al. |
|-----------|---|---|---------|----------------|
| 4,154,795 | A |   | 5/1979  | Thorne |
| 4,255,464 | A |   | 3/1981  | van der Kallen |
| 4,285,788 | A |   | 8/1981  | Eranian et al. |
| 4,299,920 | A |   | 11/1981 | Peters |
| 4,327,731 | A |   | 5/1982  | Powell |
| 4,752,855 | A |   | 6/1988  | Fedter et al. |
| 4,789,601 | A |   | 12/1988 | Banes |
| 5,026,135 | A | * | 6/1991  | Booth ........................ 385/130 |
| 5,361,625 | A | * | 11/1994 | Ylvisaker ..................... 73/38 |
| 5,483,819 | A |   | 1/1996  | Barmore et al. |
| 5,493,730 | A |   | 2/1996  | Vo-Dinh |
| 5,516,555 | A | * | 5/1996  | Felts ..................... 427/255.23 |
| 5,583,047 | A | * | 12/1996 | Blinka et al. ................... 436/5 |
| 5,608,374 | A |   | 3/1997  | Ikejiri |
| 5,639,603 | A |   | 6/1997  | Dower et al. |
| 5,773,512 | A |   | 6/1998  | Chenera et al. |
| 5,776,359 | A |   | 7/1998  | Schultz et al. |
| 5,886,126 | A |   | 3/1999  | Newkome et al. |
| 5,886,127 | A |   | 3/1999  | Newkome et al. |
| 5,891,737 | A |   | 4/1999  | Baindur et al. |
| 5,985,356 | A |   | 11/1999 | Schultz et al. |
| 6,004,617 | A |   | 12/1999 | Schultz et al. |
| 6,030,917 | A |   | 2/2000  | Weinberg et al. |
| 6,034,775 | A |   | 3/2000  | McFarland et al. |
| 6,040,193 | A |   | 3/2000  | Winkler et al. |
| 6,044,212 | A |   | 3/2000  | Flavin et al. |
| 6,432,516 | B1| * | 8/2002  | Terasaki et al. .......... 428/195.1 |

(Continued)

FOREIGN PATENT DOCUMENTS

| JP | 405253535 A   | 10/1993 |
|----|---------------|---------|
| WO | WO 90/03860   | 4/1990  |
| WO | WO 95/07764   | 3/1995  |
| WO | WO 9847613 A1 | 10/1998 |
| WO | WO 99/25750   | 5/1999  |
| WO | WO 00/17413   | 3/2000  |
| WO | WO 01/32320 A1| 5/2001  |
| WO | WO 01/33211 A1| 5/2001  |
| WO | WO/2004/077006| * 9/2004 |

OTHER PUBLICATIONS

Kumar, R.S., et al., "Low moisture permeation measurement through polymer substrates for organic light emitting devices", Thin Solid Films, vol. 417, Issue 1-2, Sep. 30, 2002, pp. 120-126.*

Jang, Jyongsik, et al., "Oxygen barrier properties of biaxially oriented polypropylene/polyvinyl alcohol blend films", Polymer □□vol. 45, Issue 5, Mar. 2004, pp. 1599-1607.*

(Continued)

*Primary Examiner*—Bret Chen
(74) *Attorney, Agent, or Firm*—Scott R. Hansen; Fulwider Patton LLP

(57) ABSTRACT

A method of developing a new coating having a desired performance characteristic with regard to a property of a coating is provided. The method includes the steps of: a) providing an array of coating wells, each well configured for receiving a coating material having a known parameter; b) placing a coating material having the known parameter in each coating well, varying the parameter so as to provide a plurality of coating material having different parameter values in a plurality of coating wells; c) correlating the value of the parameter for the coatings deposited in each of the plurality of coating wells with the position of the coating well in the array, whereby a parameter value is associated with each coating well position in the array; d) applying a coating leveling force to the array of coating wells to level the coating material in the coating wells; e) testing the coatings in the array to analyze the relationship between the position in the array and performance with regard to the property of the coating material, whereby the value of the parameter can be correlated to the performance of the coating with regard to the property of the coating. Optionally, the coatings in the array may be dried while the leveling force is applied. The above combinatorial, high-throughput method of screening candidate coat materials results in a substantial increase in the discovery rate of new coating materials. The moisture barrier characteristics of a film may be determined by providing a vapor sensitive color changing layer, with the film to be measured overlying the vapor sensitive layer, exposing the film to the vapor, and subsequently measuring the color changes.

14 Claims, 10 Drawing Sheets

U.S. PATENT DOCUMENTS

| | | | |
|---|---|---|---|
| 6,597,753 B1 * | 7/2003 | Okayasu et al. | 702/39 |
| 6,684,683 B2 * | 2/2004 | Potyrailo et al. | 73/24.06 |
| 7,157,147 B2 * | 1/2007 | Inui et al. | 428/451 |
| 2004/0012107 A1 * | 6/2004 | Urscheler et al. | 427/420 |
| 2005/0079380 A1 * | 4/2005 | Iwanaga | 428/688 |
| 2006/0093742 A1 * | 5/2006 | McGlinchy et al. | 427/258 |
| 2006/0169026 A1 * | 8/2006 | Kage et al. | 73/38 |

OTHER PUBLICATIONS

Taylor, S. Ray, "Assessing the Moisture Barrier Properties of Polymeric Coatings using Electrical and Electrochemical Methods", IEEE Transactions on Electrical Insulation, vol. 24, No. 5, Oct. 1989, pp. 787-806.*

Raimundo Jr. et al.; Evaluation of Nafion-Crystal Violet films for the construction of an optical releative humidity sensor, The Analyst, 199, 124, pp. 1623-1627.

Otsuki, et al., A novel fiber-optic gas-sensing configuration using extremely curved optical fibers and an attempt for optical humidity detection; Elsevier; Sensors and Actuators B 53 (1998), pp. 91-96.

Yutaka Amao, Keisuke Asai, Ichiro Olura, Hiromi Shinohara, and Hiroyuki Nishide; "Platinum Porphyrin Embedded in Poly(1-Trimethylsilyl-1-Propyne) Film as an Optical Sensor For Trace Analysis of Oxygen"; *The Analyst Communication*, 125, pp. 1911-14; Oct. 12, 2000.

Machevskaya, R.A., Sharapova, I.A., Karaseva, T. M., Tsyganova, M. P., Shuvalova, A. I.; "Study of the Interrelation of Properties of Coatings and the Compostion of Epoxy-Phenol Compositions", *Lakokras. Mater. Ikh Primen* (1), pp. 35-36; 1981.

* cited by examiner

HIGH THROUGHPUT SCREENING FOR MOISTURE BARRIER CHARACTERISTICS OF MATERIALS

RELATED APPLICATION

This application is a continuation-in-part claiming priority to previously filed PCT patent application Ser. No. PCT/U.S.00/29854 filed Oct. 30, 2000 and PCT patent application Ser. No. PCT/U.S.00/29990 filed Oct. 30, 2000, which both in turn claim priority from prior U.S. Provisional Patent Application Ser. No. 60/162,349 filed Oct. 29, 1999.

BACKGROUND OF THE INVENTION

1. Field of the Invention

The invention relates generally to methods and apparatus for identification and optimization of coating materials and properties for desired applications. More specifically, the invention relates to an improved process of creating coatings, involving identifying candidate materials and screening and optimizing formulations and coating parameters for desired applications, for example the measurement of the moisture barrier properties of films.

2. General Background and State of the Art

Development of coating materials, for example adhesive coatings, release coats, protective coatings, and the like as well as films and laminate constructions of layered materials, has conventionally been a time consuming and labor intensive process. Candidate materials are identified primarily based on knowledge and experience with what compositions have worked before in related applications and investigating like materials and combinations of materials. This usually involves preparing a coating formulation, preparing a test coating for evaluation (often involving several tries to attain the desired parameters such as coat weight, cure, etc. for evaluation), drying the coating, then evaluating the coating by testing the property of interest, such as permeability, tack, shear, bending strength, surface roughness, etc., and entering the results in a database for comparison with further coatings to be developed and tested. Problems of cross-contamination and holdover further limit the number of formulations that can be screened in a given time period. This is a time-consuming process and as a result one skilled in the art, even with support staff to assist and carry on tasks in parallel, has conventionally been able to screen at most a few coatings per day, most often only one or two.

Because of the lengthy time required to screen and then investigate candidate materials and associated coating application parameter values to select and optimize coatings, those skilled in the art generally must focus on families of materials known to possess properties likely to prove successful in the intended use. Investigation of unconventional or simply previously untried materials is usually limited. Moreover, development of coating materials for a particular application is also a time-consuming process, and development of new coatings, while potentially beneficial, sometimes cannot be pursued due to economic considerations arising out of the time and effort involved.

Requisite in the development of new coating materials is the use of a particular coating method as well as consideration of holdover or carryover effects. Holdover effects result in the contamination of one candidate coating material due to residual coating material remaining in the coat dispensing apparatus and/or coat-receiving substrate from a prior test coating material. Contaminations as a result of holdover effects are generally additive and provide a level of error in coat formulation that is difficult to control. It is therefore preferable, especially when the volume of coating material to be tested is small, to use a coating method that either eliminates or significantly reduces holdover effects. Use of a disposable method for dispensing as well as receiving the test coat material would eliminate problems associated with holdover effects.

A variety of methods for coating desired substrates or materials are available and include spin coating, die coating and non-contact jet coating methods. Spin coating is a technique commonly used in the field of electronics where the coat material is dispensed onto a spinning plate where it is spread by centrifugal force. The coatweights resulting from this method are limited to very thin coatings and there is a significant loss of material during the coating process. In both the die coating and non-contact jet coating methods, die and jetting nozzle costs prohibit their modification to disposable units. Prior to the instant application, an inexpensive, efficient and disposable method for testing a large number of coating materials has not been known. While many significant advances in coating technology have been made in recent years, acceleration of the rate at which coating materials can be identified, screened, investigated and optimized will be recognized as a desirable goal by those skilled in the art.

INVENTION SUMMARY

An object of the invention is to provide a multi-well apparatus for making arrays of coating materials. Such arrays are suitable for analysis and may comprise a disposable two-layer assembly where the first layer contains a plurality of wells and the second layer is a substrate layer. Both layers can be flexible, with the second or bottom layer being detachable from the overlying first layer. Such an apparatus can be made of disposable material, thus providing a cost-effective, efficient and reliable means of making and testing numerous formulations of coating material.

The invention also provides a method of developing a new coating having a desired performance characteristic with regard to a property of a coating, comprising: a) providing an array of coating wells, b) placing a coating material having the known parameter in each coating well, varying the parameter so as to provide a plurality of coatings having different parameter values in a plurality of coating wells; c) correlating the value of the parameter for the coatings deposited in each of the plurality of coating wells with the position of the coating well in the array, whereby a parameter value is associated with each coating well position in the array; d) applying a leveling force to the array of wells to level the coating material in the coating wells; and e) testing the coatings in the array to analyze the relationship between the position in the array and performance with regard to the property of the coating material, whereby the value of the parameter can be correlated to the performance of the coating with regard to the property of the coating. Optionally, the coatings in the array can be dried or cured while the leveling force is applied. The above combinatorial, high-throughput method of screening candidate coat materials results in a significant increase in the discovery rate of new coating materials. In a preferred embodiment the leveling force may be provided by a centrifuge.

One of many possible characteristics that may be desirable in a new coating or film formulation is the vapor barrier characteristics/vapor transmission rate of various materials to various vapors. As an example, the present invention provides apparatus and associated methods of use that allow for high throughput screening and identification of moisture barrier properties of coatings and/or films. Therefore, in accordance with the functional aspects of the composition and construction of exemplary illustrative embodiments of the present invention, a vapor transmission sensor is provided comprising a film, or substrate, upon which a vapor sensitive coating is placed. Furthermore, after depositing the vapor sensitive coating on one side of the film, the coating formulations to be tested are disposed onto the opposing side of the film. Once the coating formulations to be tested are so placed, the film, now with the vapor sensitive coating on one side and the coating formulations to be tested on the other, is laminated onto a transparent backing that displays a high barrier characteristic to the vapor of interest. The side having the vapor sensitive coating is mounted so as to be sandwiched between the film and transparent backing. By assembling the exemplary vapor transmission sensor in this manner, the vapor of interest is limited in its interaction with the vapor sensitive coating.

There are two routes by which the vapor of interest will interact with the vapor sensitive coating located between the film and the transparent backing. The first route is a "direct" route. In this instance, the vapor of interest only has to pass through the film or substrate portion of the vapor transmission sensor. After passing through the film, the vapor of interest interacts with the components of the vapor sensitive coating. As a consequence of these interactions, the vapor sensitive coating undergoes a chemical change that results in some measurable, quantitative change. The second, informative route, has the vapor of interest passing through the coating formulations and then through the substrate/film, where it interacts with the vapor sensitive coating, as previously mentioned. In an exemplary embodiment detailed below, this change is chromatic and is measured by recording the changing absorbance of particular, informative positions (having a material, including a coating material) of the vapor sensitive sensor over time. This will provide quantitative measurements of the barrier characteristic of each of the samples of materials.

With regard to the method and apparatus of the proposed system, in one aspect it involves utilization of a vapor sensitive film with the film or coating sample to be measured overlying the vapor sensitive film and exposing the film sample to be measured to the vapor, and then measuring changes in the vapor sensitive film. The substrate on which the films are mounted may be transparent, with the two films on opposite sides thereof; or the substrate may be opaque, with the film or coating to be measured directly overlying the vapor sensitive film, and reflection type color measurements being employed in testing the vapor sensitive film. For high throughput testing, arrays of samples may be used. The samples may be measured successively after successive exposures to the vapor; or a standard testing interval may be employed, with the testing occurring only once after exposure to the vapor for a predetermined interval of time.

Further features, details, and advantages of the invention will be more apparent with reference to the following detailed description, taken in conjunction with the accompanying drawings, which illustrate, by way of example, principles of the invention.

DETAILED DESCRIPTION OF THE PREFERRED EMBODIMENTS

In accordance with one aspect of the invention, it has been recognized that by using automation of certain development processes, miniaturization of samples to be tested, database development and manipulation, and using algorithms to identify candidate materials from information contained in databases, one can increase the number of coating materials that can be developed to meet identified needs. As used herein, the term "combinatorial" refers to the combined approach of high-throughput analysis of libraries consisting of arrays of coat material formulations. Included in the high-throughput analysis are automated or robotic processing of the sample arrays.

Combinatorial methods have been used in the medical, pharmaceutical and biotechnology industries to develop chemical compositions, particularly pharmaceuticals and medicaments, for a number of years. However, these prior combinatorial methods have not been well suited to development of new coatings. Applicants herein provide techniques for generating arrays of coating formulations, well suited to the application of combinatorial chemistry methods. These techniques allow new coatings to be screened and evaluated on a high throughput basis, in order to produce new coatings economically.

Combinatorial Approach

Figure 1:
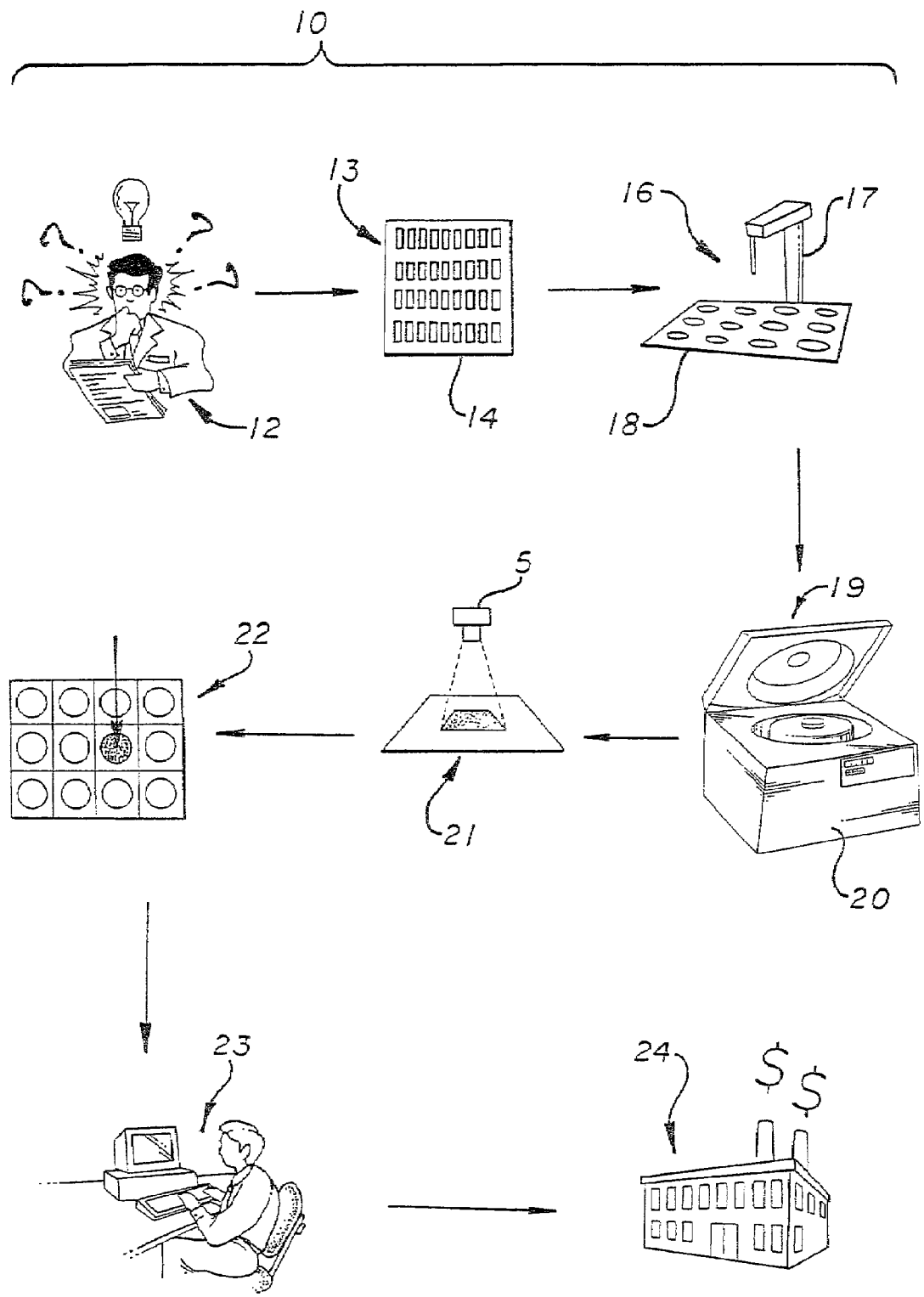
FIG. 1 is a generic schematic of the combinatorial discovery process.

With reference to FIG. 1 of the drawings, which are given by way of example, and not by way of limitation, a system 10 in accordance with principles of the invention comprises a method of developing new coatings by means of a combinatorial approach. A first step 12 is to define what end result coating is desired, and what characteristics and qualities such a coating will have. To achieve the desired result a new material, or a new construction of several materials, such as a laminate for example, comprising new and/or conventional materials combined in a novel way may be required.

At the outset it should be understood that combinatorial methods could be applied to both the process of creating coating materials by formulation or synthesis, and to creating coating parameters or desired characteristics.

Returning to consideration of one example of a combinatorial approach to coating development, the next step 13 is to select likely candidate materials. These can comprise formulations of generally solutions of raw material ingredients 14 that are contemplated as likely elements or components that may provide a coating material with desired characteristics. In the next step 16 a material library of a few to a few hundred thousand, or more, chemical combinations are formed and dispensed into an array of coating wells 18 using a robot or other automated device 17 to make a library or array of coating materials. Incidentally, the "libraries" may include the samples in a single array, or the samples may form a plurality of arrays, processed either concurrently or successively. The chemical combinations forming at least part of the library are then processed in parallel as indicated at reference numeral 19. Processing can include exposing the coating array to a variety of processing variables such as heat, and time as well as applied leveling forces to shape the resultant library or array of coat samples, as can be accomplished, for example, by a centrifuge 20. In the next step 21 high throughput analysis is performed whereby the library is screened by detectors that quickly scan various properties of the coating materials. After the high throughput analysis, materials with the desired properties are identified 22 with the results entered into a large database 23, allowing many variations of materials to be tested at one time. Each library is comprised of one or more arrays of variations of materials to be tested. Each individual site in an array will correspond to a specific formulation of a coat material, wherein the parameter or coat descriptor(s) of the material located at that site is known. Miniaturization of the sample size facilitates processing and greatly saves cost and time thereby increasing efficiency and the rate of discovery. The end result is discovery and determination of the most successful new material(s) and the process or parameters used to produce the new materials. These materials are then selected for large scale production and commercialization 24.

As an example, a parameter that may be of particular interest is the vapor barrier characteristics of newly formulated material(s). The barrier characteristics of these materials to a vapor of interest, or, similarly, the transmission rates of particular vapors, through various materials and/or coatings are important functional aspects of materials utilized in various applications.

As an example, plastic materials tend to be permeable to various vapors or gases, including water vapor. For materials, including coating materials, that are used in packaging and electronic components, low permeability to vapors is a characteristic that is often preferred. In one embodiment of the present invention, a multi-layered assembly is provided that provides users a method to characterize and test the rates of vapor transmission through sample formulations of material, including coatings and films. In the particular embodiment detailed herein, the present invention provides an efficacious method for high throughput screening of a plurality of materials, including coatings and films, to determine their barrier properties to vapors/gases, and similarly the rates of transmission of these vapor(s) of interest through the samples of materials. A detailed description of the design of an exemplary multi-layered apparatus is provided below.

The combinatorial approach to development and testing of novel coat materials greatly benefits from use of devices and apparatus that allow flat coating samples in the arrays or within wells in the arrays. Additional embodiments encompassing such devices and apparatus are included in the present invention and further described below.

Figure 2:
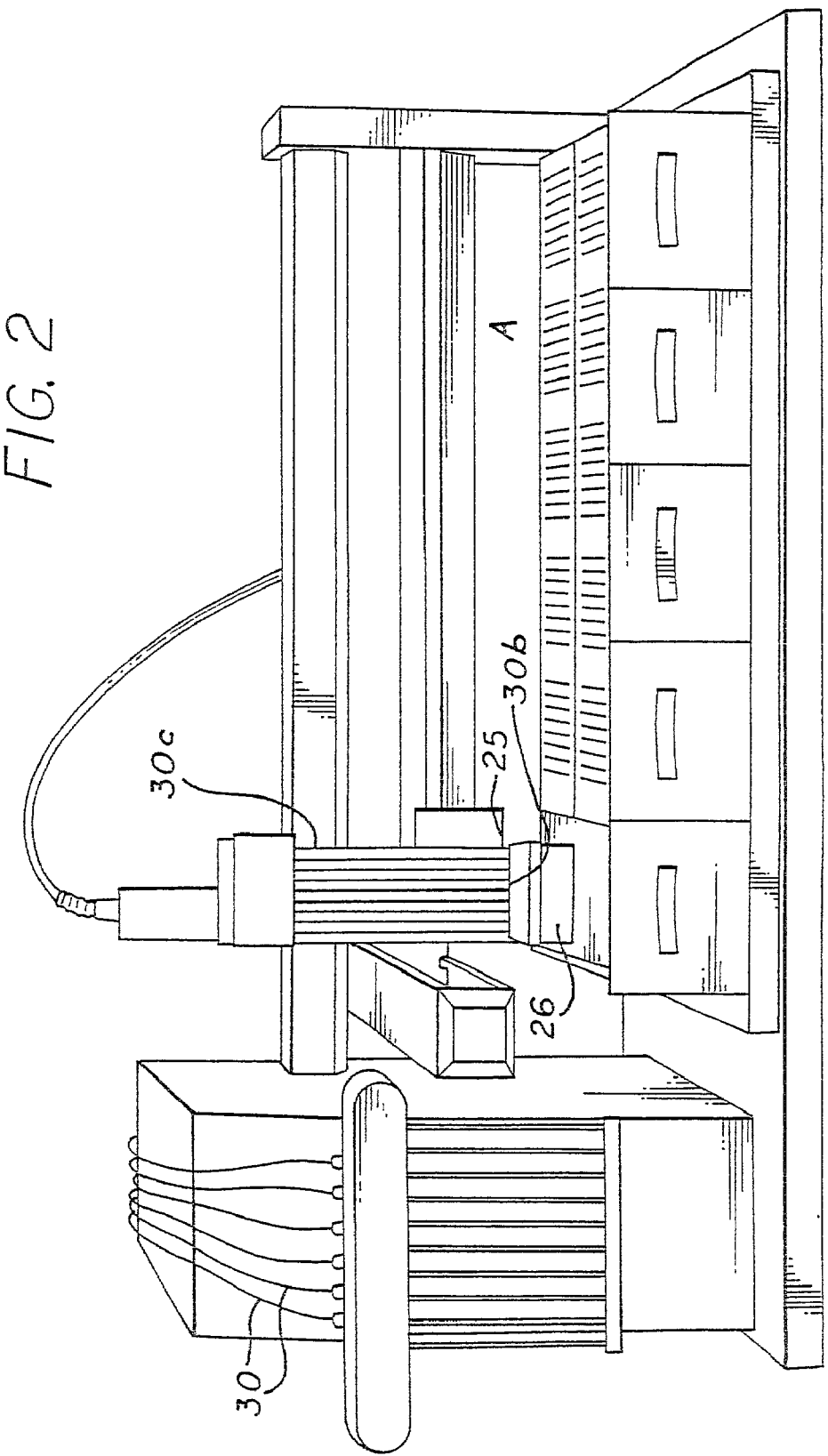
FIG. 2 is a perspective view of an example of a robotic dispenser usable in one embodiment of the invention.
Figure 3:
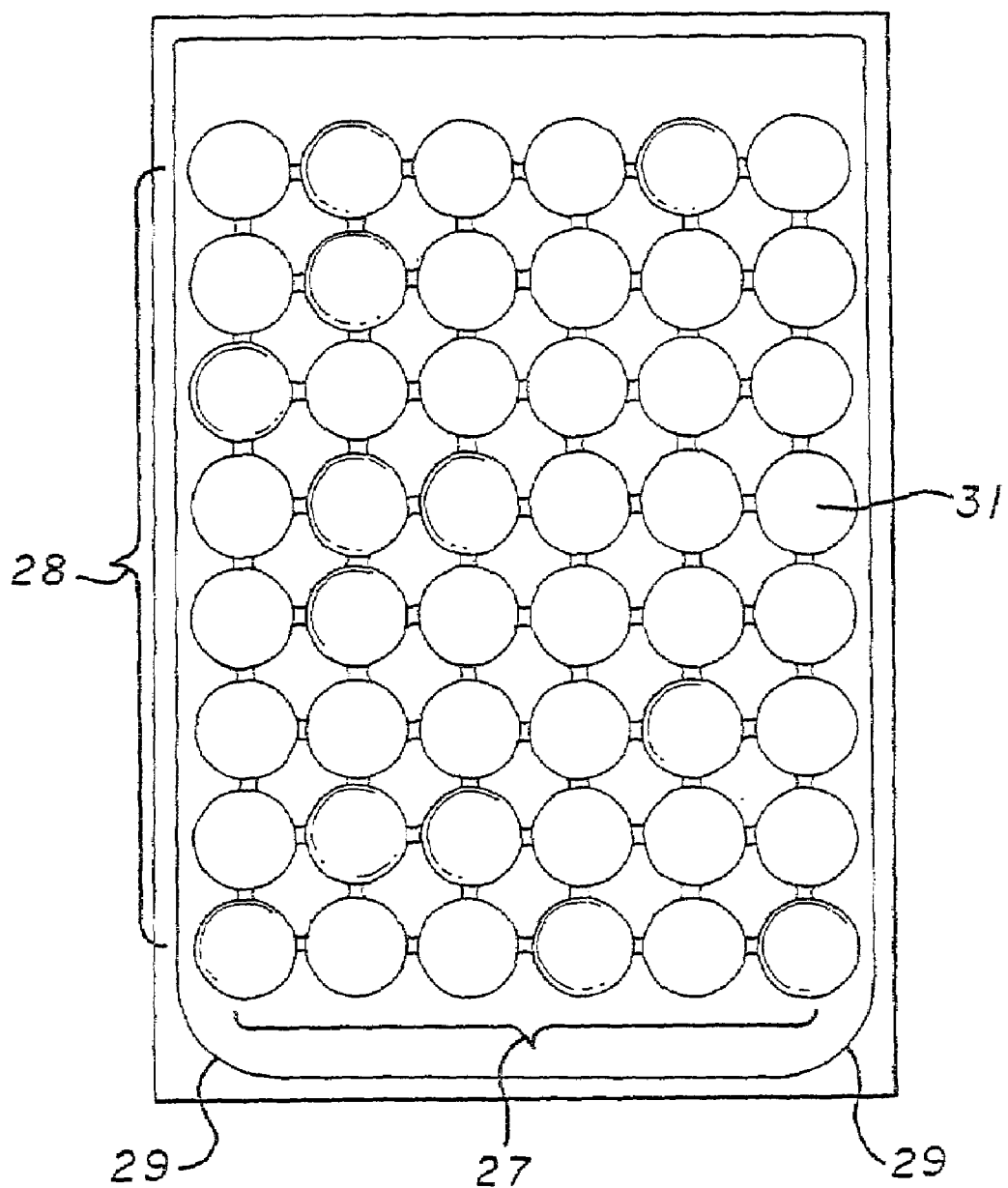
FIG. 3 is a top view of an example of a well plate usable in one embodiment of the invention.

When trying to coat one formulation after another in a rapid fashion using conventional equipment, "holdover" considerations are important. As used herein, the term "holdover" is defined as the volume of material that is residual in a cavity after it is emptied and could contaminate the next batch of material deposited into the cavity. As volumes of the cavity get smaller, the potential for holdover increases. For example, tubes, pipette tips, material dispensers and such all have potential holdover volumes. The contamination is also a function of the rheological nature or viscosity of the material that is deposited into the cavity. Holdover effects in traditional methods of developing coating materials greatly increases the level of error, compromising the identification of correct parameters of a new coat material. In the present invention, holdover and its contaminating effects are eliminated by use of a disposable dispensing device 25, such as disposable pipettes or disposable pipette tips, for example (FIG. 2) and a disposable substrate assembly (formatted as a multi-well apparatus) 26, both of which are further described below. As used herein, the term "substrate" is defined as any coat-receiving surface or material, or a substance upon which a sample coat material resides which allows the testing of that sample. A "substrate assembly" is a composite of materials formed into a unit or apparatus for holding a large number of different coating samples in an array format (FIG. 3). An "array format" as used herein, is a matrix format where the samples of coating material are arranged as discrete coated areas 31 on a surface, such as a planar surface. For example, a 48-well coating array (FIG. 3) would have 48 discrete coated areas arranged as 6 rows 27 and 8 columns 28.

Multi-well Apparatus for Parallel Processing of a Material Library

An initial step in the development of a coating is to create the various mixed formulations to be placed in the wells in the array. In one embodiment of the present invention, such sample formulations can be mixed or prepared in a multi-well plate format (FIG. 3) with each individual well containing a unique, pre-defined formulation to be tested. A variety of types of commercially available multi-well plates suitable for use in the present invention can be used (Millipore Corp., Polyfiltronics, VWR Scientific). Such multi-well plates can vary in size of plate dimension, size of well (outer circumference as well as well-depth), type of material used to construct the multi-well plate (for example, polystyrene or polypropylene, rigid plastic or flexible plastic). The biotechnology and pharmaceutical industry utilizes multi-well plates (generally 48-, 96- or 384-well plates) whose outer dimensions are standardized for use with automated equipment. Exemplary, standardized multi-well plates are rectangular, rigid, stackable plates with right edges of the top or lid portion being curved 29. The outside dimensions of a complete multi-well unit are approximately 5×3.25 inches. Such multi-well plates are suitable for use in the present invention. In general, the well size used should be of substantial volume so as to allow adequate robotic mixing of the required or needed amount of each formulation. Preferably a well volume of 0.5 to 3 cubic centimeters in volume is contemplated for use in the present invention. The minimum quantity or volume of sample to be mixed in a "mother" wellplate will vary depending upon the intended uses for the library.

As used herein, a "mother" well plate is defined as a source well plate. For example, a 25 micron thick coating that is 1 $cm^2$ in domain size with a coating solution that is 50% solids, will require (1 $cm^2$×25 microns/0.5) volume units or 0.0050 cc of solution. "Domain size" as used herein, refers to the minimum area required for the coated sample as determined by downstream testing. The appropriate volume of individual formulations from this mother well plate can then be dispensed to a sample or "daughter" well plate to make a coating with the desired domain size for subsequent analysis and data collection. It should be understood, that alternative embodiments include use of a single well plate as both the mother and daughter well plate. In such a case, the well plate into which the sample formulations are mixed will also serve as the well plate from which the coating materials will be tested. Again, considerations of desired coating thickness, domain size and formulation of coating solutions will be included in determination of minimum volume of well size required. Additional embodiments of well plate apparatus design will be discussed further below.

Automated Dispensing of Candidate Coat Materials for Testing

A disposable metering device can be used to dispense the formulations from a mother well plate to a daughter well plate. A robotic dispenser (available commercially for example, from Hamilton, Zinser, or Packard) (FIG. 2) is one such device. Robotic dispensers allow for rapid and automated dispensing of a specified quantity of a large number of samples. The well plate format to be used for the daughter well plate will also depend on the domain size requirement of the coating. For example, a 6-, 12-, 24-, 48-, 96-, or 384- well plate format are commercially available formats which can be used in the present invention with the commercially available robotic dispensers. The robotic dispenser will have a platform area upon which the substrate well plates reside (FIG. 2; "A").

Alternatively, in the case where a single well plate is used as both the mother and daughter wellplate, a robotic device can also be used for mixing as well as dispensing component materials for the sample coating formulation to be tested. Such a device could have multiple dispensing units 30 from which specific and precise amount of an individual component is dispensed into a single well. The sample solution can be dispensed using disposable pipette tips 30b attached to the pipettors 30c. For example, a separate dispensing unit for each component can be used to dispense the appropriate amount of a respective component into a single sample well. Such a dispensing unit can be disposable which will allow rapid and accurate automation of the combinatorial method for formulating or synthesizing a new coating with elimination of holdup or contamination problems. Examples of disposable dispensing units include, polyethylene or other type of tubing and disposable pipette tips.

Alterative Designs of Multi-well Apparatus for Parallel Processing

Figure 4:
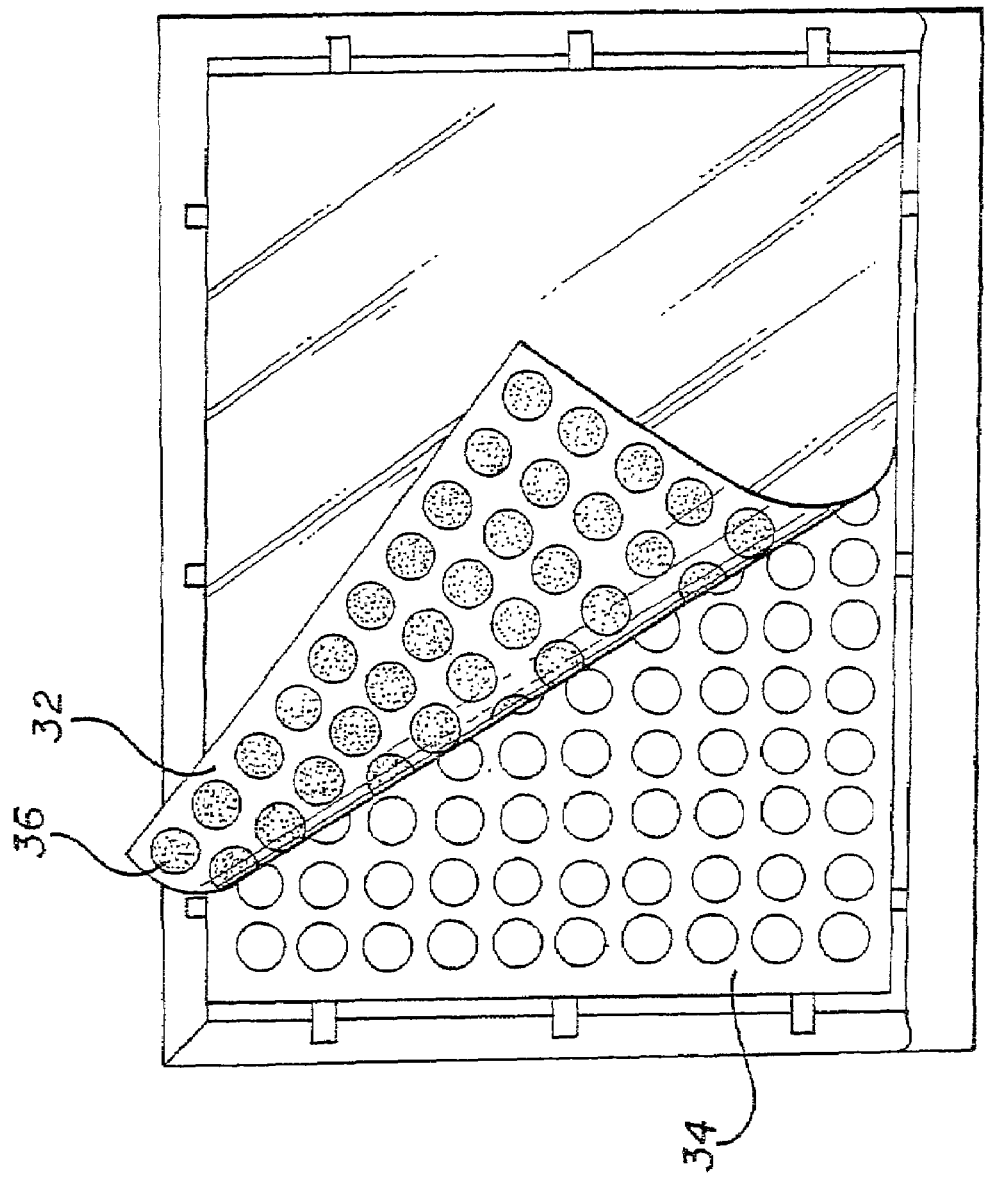
FIG. 4 is a perspective view of an example of a well plate having a removable well bottom, comprising a substrate to which sample coatings are applied, usable in one embodiment of the invention.
Figure 5:
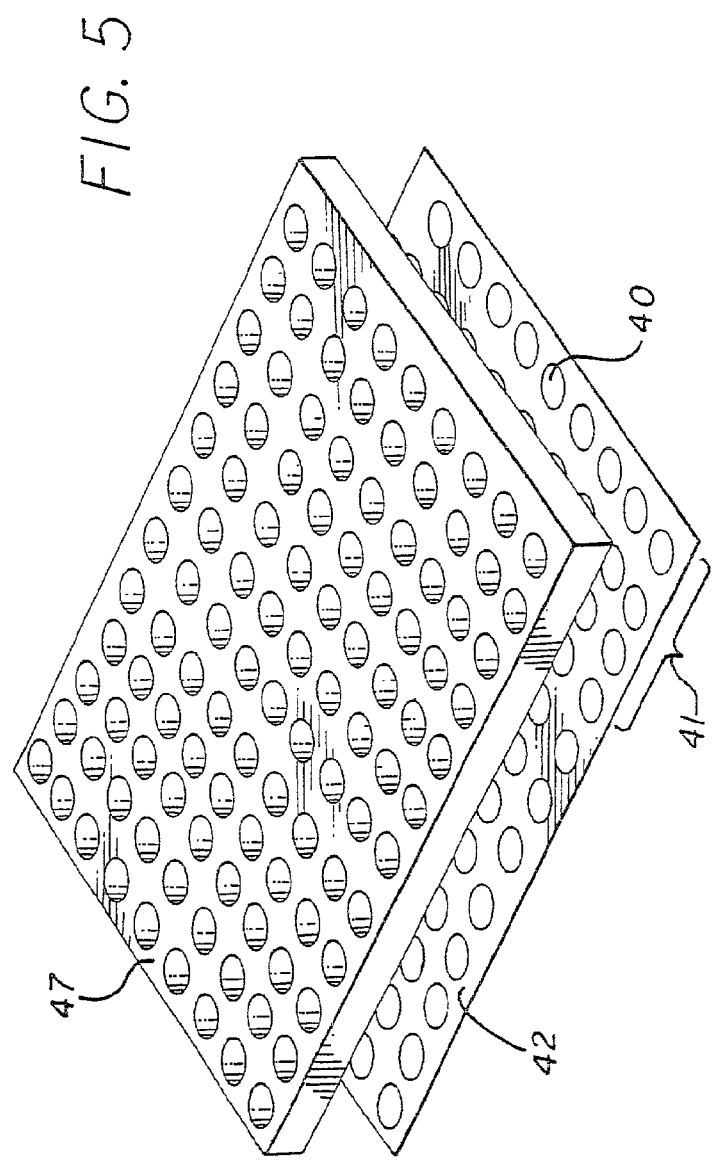
FIG. 5 is a perspective view of another example of well plate having a removable well bottom comprising a substrate to which sample coatings are applied, usable in one embodiment of the invention.
Figure 7:
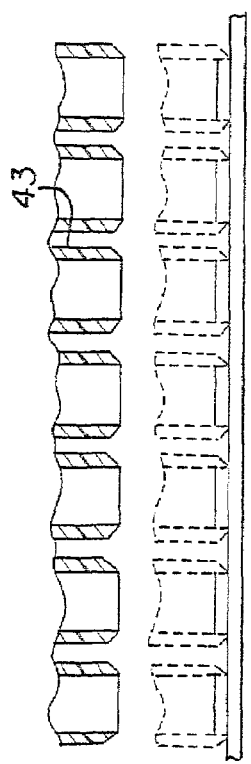
FIG. 7 is a side view of a flexible well plate having a removable top portion usable in one embodiment of the invention.

Alternative embodiments of well plate design include providing a two-piece coating well apparatus having at least a substrate portion 32 and a multi-well or sample-containing template 34 which can be separated from one another (FIG. 4). Once leveled and dried, the coating material 36 is held by the substrate portion 32 of the assembly. This type of well plate assembly is designed such that the base substrate-portion (or bottom half of the assembly) 32 can be removed from the multi-well template portion 34 of the well plate assembly. Various embodiments of a well plate design having a removable bottom are contemplated and further described below. FIG. 5 shows an example of a multi-well plate depicting the array format useful in the invention. Coating material samples are placed within the apertured, multi-well template top 47. Such multi-well plates will form an array 41 or library of the different formulations as discrete coated areas 40 on a planar substrate sheet 42. A multi-well plate with a removable top or cover can also be used as a well plate assembly. An example of such a multi-well plate design is shown in FIG. 7. The well plate design can also include modifications to the well plate to prevent distribution of coating material onto the inner walls of the wells. For example, a release coating can be applied to the inner walls 43 of the wells to prevent any sample material from moving up and onto the well walls during application of a leveling force.

Figure 6:
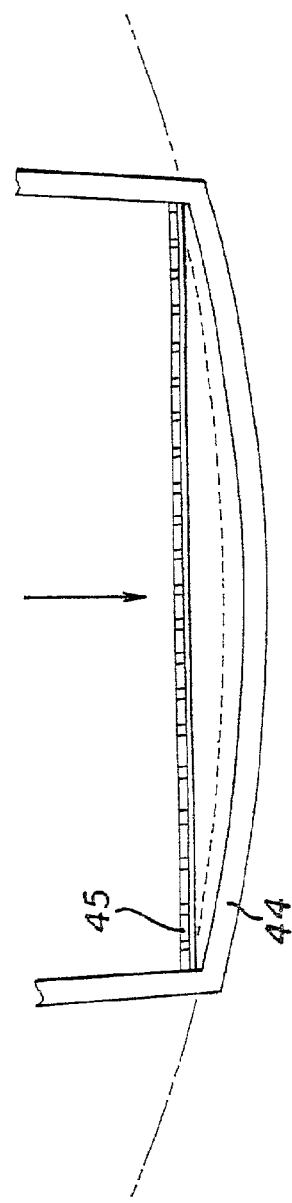
FIG. 6 is a side view of a well plate having a curved bottom usable in one embodiment of the invention.
Figure 18:
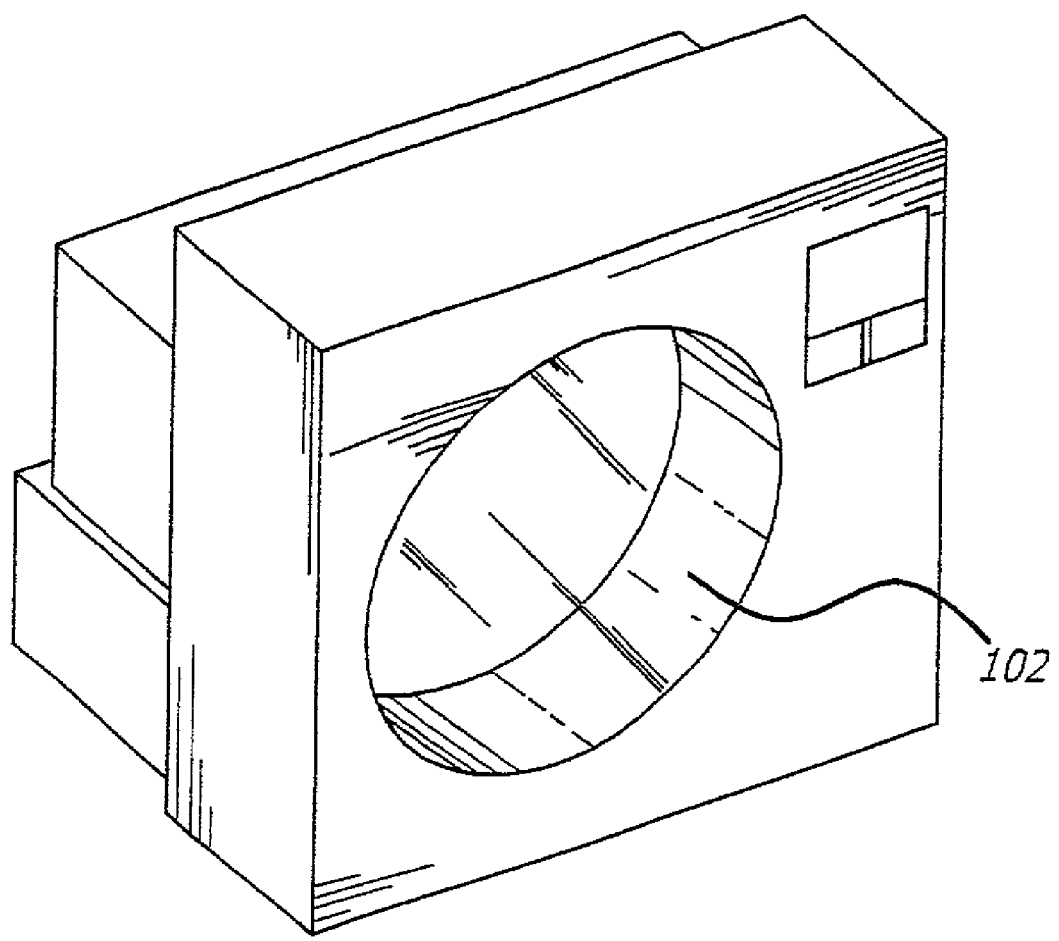
FIG. 18 is an exemplary illustration of a centrifuge with a horizontal axis of rotation and curved, rotating surface upon which multi-well apparatus and laminate well plate constructions may be mounted.

An additional embodiment of the present invention includes multi-well plates designed to obtain flat coatings in all of the wells of the assembly. Current commercially available multi-well plates have a flat-bottom surface for the entire plate. This results in an uneven distribution of sample material in the wells located along the perimeter of the multi-well plate 68 when current swing arm type of centrifuge rotors 70 are used to apply a leveling force. FIG. 6 shows an example of a modified multi-well plate designed to obtain flat coatings in all of the wells. Such a well plate will have a curved base plate 44 where the curvature of this base is parallel to the circumference of the centrifuge rotor, or is curved so as to substantially match the curvature of the curvilinear path of the well plate during centrifugation. With a curved-bottom well plate 44, sample material or coating solutions in all of the wells, including perimeter wells 45, will be at the same distance from the spin axis of the centrifuge. Thus, coating material in all of the wells will have a flat distribution following centrifugation. The top view of such a multi-well plate can be as depicted in FIG. 5. A flexible substrate and apertured well plate may be employed to provide a curved configuration when mounted in a centrifuge. The centrifuge of FIG. 18 is one that is particularly useful in light of the teachings of the present invention. Here, this centrifuge has a "rotating drum-type" configuration. The axis of rotation is horizontal, similar to a front loading clothes dryer, and the flexible substrate and apertured well plate may be mounted onto the centrifuge's curved, rotating surface 102.

Figure 8:
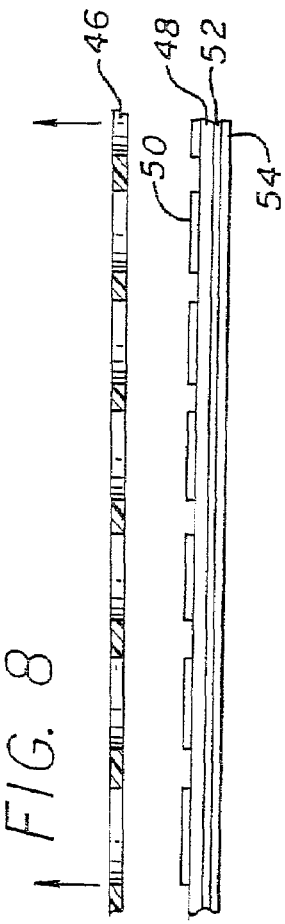
FIG. 8 is a side view of a well plate having a laminate construction usable in one embodiment of the invention.
Figure 10:
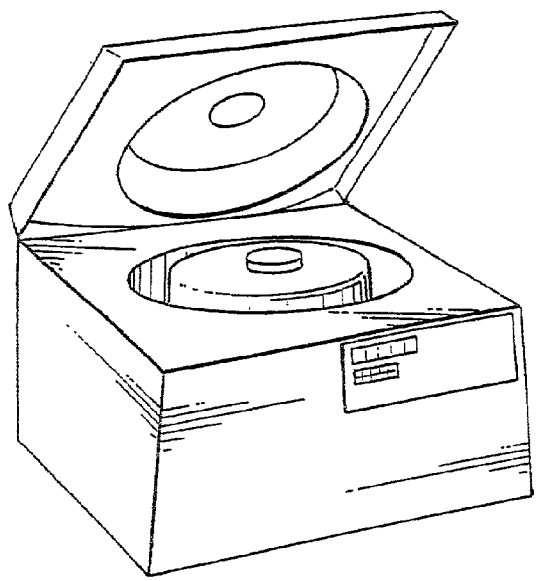
FIG. 10 is a perspective view of an example of a centrifuge usable in an embodiment of the invention.

A specialized laminate well plate construction is also envisioned as an alternative embodiment of the present invention. FIG. 8 shows a cross sectional view of a representative laminate multi-well plate assembly. In one case, the assembly is made up of at least 4 layers and is shown in FIG. 8. The top or first layer 46 corresponds to the multi-well or sample holding portion of the assembly. This layer need only be thick enough to provide a sufficient barrier between adjacent wells so that the dispensed coating material 50 does not cross contaminate adjacent samples. Where a very small amount of coating material 50 is to be tested, this layer need not be very thick and could be made of, for example, thin plastic, foam or paper with each well formed of holes placed in linear, multiple rows to form an array pattern. Preferably, the top layer will be about 0.01 to about 1 mm, or about 1 to about 10 mm, or about 1 to about 5 cm in height. This top layer 46 can be coated with a Pressure Sensitive Adhesive (PSA) (not shown) to attach it to the substrate layer 48. This will also help to seal the wells so that cross-contamination of sample coating material from one well does not mix with its neighbors. The second layer is the substrate layer 48 and can be formed of a variety of materials, such as plastic, polymeric resin or paper, so long as it will hold the sample coating material 50 in a flattened manner. The second layer will preferably be about 10 to about 1000 microns, or about 1 to about 10 mm, or about 1 to about 5 cm in thickness. The third layer is a Pressure Sensitive Adhesive layer (PSA) 52. The PSA layer 52 can be about 5 to about 100 μm, or about 0.005 to about 0.1 mm, or about 0.0005 to about 0.01 cm in thickness depending upon the type of adhesive and degree of adhesion desired. The fourth layer is a liner 54 coated with a release layer such as silicone, which can be removed or peeled away from the PSA layer 52 leaving the adhesive on the bottom of the substrate layer as the new bottom layer. This type of multi-well plate design is suitable for example, where the stickiness or tackiness of a coating material is to be tested. In such a case, it is desirable to have an array library which will remain stationary or adhere to a support surface by the PSA layer 52 while each individual coating sample is tested. Use of the PSA 52 on the layer 48 will allow the array library to remain stationary and not lift up during testing.

In an additional embodiment, in accordance with the teachings of the present invention, a multi-well plate design (multi-layered assembly) is provided that is useful in the determination of a material's barrier properties to various vapors/gases. As mentioned previously, the measurements provided may also be utilized to determine a vapor's transmission rate through a sample of a material, such as a coating or film.

In order to assess the barrier properties of a sample coating or film material, another specialized laminate multi-well plate is provided, the construction of which is herein disclosed. In an exemplary construction, a multi-layered assembly is configured to ascertain the barrier properties/vapor transmission rates of water vapor through sample coating materials and/or films.

Similar methodologies, detailed in this specification, of providing arrays of sample materials, including coatings and films, on a substrate 32 are utilized in the formation of the multi-layered assembly to ascertain the barrier properties/vapor transmission rates of water vapor through sample coating materials and/or films.

Figure 13:
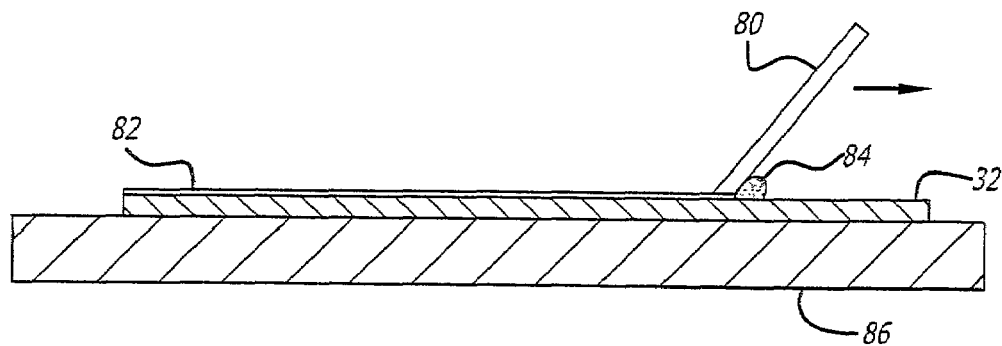
FIG. 13 is a cross-sectional view of the preparation of a vapor sensitive film, or vapor sensor, depicting the coating of a vapor sensitive mixture on one side of a substrate.

In order to provide a substrate 32, upon which the barrier properties/vapor transmission rates of water vapor through sample coating materials and/or films may be determined, we turn to FIG. 13. The substrate 32 portion of the multi-layered assembly is illustrated in FIG. 13, which is a cross-sectional view showing the preparation of a vapor sensitive film, depicting the coating of a vapor sensitive mixture on one side of a substrate 32. This vapor sensitive film (or vapor sensor), which is comprised of a substrate 32 and a vapor sensitive composition 82 thereon coated, in this example is sensitive to water vapor, and is formed by the following exemplary manner.

Still referring to FIG. 13, a substrate 32 is provided. Substrate 32 can be comprised of various material, as detailed previously and below. As an example, substrate 32 may be a piece of film, comprised of polyethylene terephthalate (PET) film, of about 0.001-0.003 inch thick, for example. Substrate 32 is placed onto a flat surface 86 in order to prepare the upward facing portion of substrate 32 for coating with a water vapor sensitive composition 84. Flat surface 86, may be comprised of wetted glass as well as other transparent material. When utilizing glass as the flat surface 86, substrate 32 is placed upon flat surface 86 and leveled flat with a paper towel, for example, making sure to remove any wrinkles in substrate 32 or bubbles situated between substrate 32 and flat surface 86. This secures substrate 32 to flat surface 86, providing an even coating surface to which a water vapor sensitive composition 84 is applied.

An exemplary formulation for a water vapor sensitive composition that is utilized to coat one side of substrate 32 is comprised of methanol, water, crystal violet and Nafion®. Crystal violet is a cationic dye that contains three N-phenyl terminal groups and is frequently utilized as an acid-base indicator that undergoes a color change. Nafion® (E. I. du Pont Nemours, Wilmington, Del., USA) is a perfluorosulfonate ion exchange polymer and commercially available in a 5 wt. % solution in aliphatic alcohols and 10% water.

An exemplary solution of methanol, water, crystal violet and Nafion®, that, when coated onto substrate 32 effectively makes substrate 32 into a water vapor sensor, is prepared as follows. A crystal violet solution having a concentration of about 0.015 M in methanol is prepared, making sure all of the crystal violet crystals have dissolved. About 52 mls of this solution is mixed with about 76 mls of Nafion® solution (Aldrich 27,470-4) and about 15 mls of water. This gives rise to a coatable water vapor sensitive composition 84 depicted as being coated onto one side of substrate 32 in FIG. 13. A front of vapor sensitive composition 84 is being passed over the surface of substrate 32 by a coating device 80, leaving behind a coating or film of the water vapor sensitive composition 82. Coating device 80 may be a Byrd bar, which are devices that are well known to those skilled in the coating arts as devices utilized to spread or coat various materials onto surfaces at a specified thickness. An exemplary thickness of a coating of the water vapor sensitive composition 82 on the substrate 32 is of about 5-6 mils.

The coating of the water vapor sensitive composition 82 is allowed to dry. Once dry, a phase inversion occurs with the Nafion® polymer and crystal violet dye, entrapping the dye in an ionic cluster. Nafion® has highly acidic sulfonate groups which place the crystal violet dye in that acidic environment. The acidity of the protons in Nafion®'s sulfonate groups depends on the water content in the film or coating of water vapor sensitive composition 82. When the film of water vapor sensitive composition 82 is dry, the acidity of Nafion® is high. This results in the crystal violet displaying a diprotonated form, imparting a yellowish color to the coating of the water vapor sensitive composition 82. However, with increasing water content of the film of water vapor sensitive composition 82, the sulfonate groups become less acidic and the diprotonated crystal violet loses its protons, which consequently changes the color of the water vapor sensitive composition 82 to a bluish color. It is this color change, or absorbance at specific wavelengths, over time, that is utilized in the determination of the barrier properties/vapor transmission rates of materials, including sample coating materials and/or films.

It is important to note that the vapor-sensitive material herein disclosed is an exemplary formulation for the determination of the transmission rate and/or barrier properties of films and coatings. While the presence and/or transmission of the vapor of interest is, for example, indicated by exemplary absorbance measurements, optical measurements other than absorbance may also be utilized; and other indicator dyes, as known in the art may be employed. Similarly, it should be noted that utilization of Nafion® and crystal violet is exemplary, and that other polymers, organic dyes (crystal violet or another light absorbing dyes), as well as other organic dye compositions available for utilization in the present invention, alone or in combination, may also be utilized.

Figure 14:
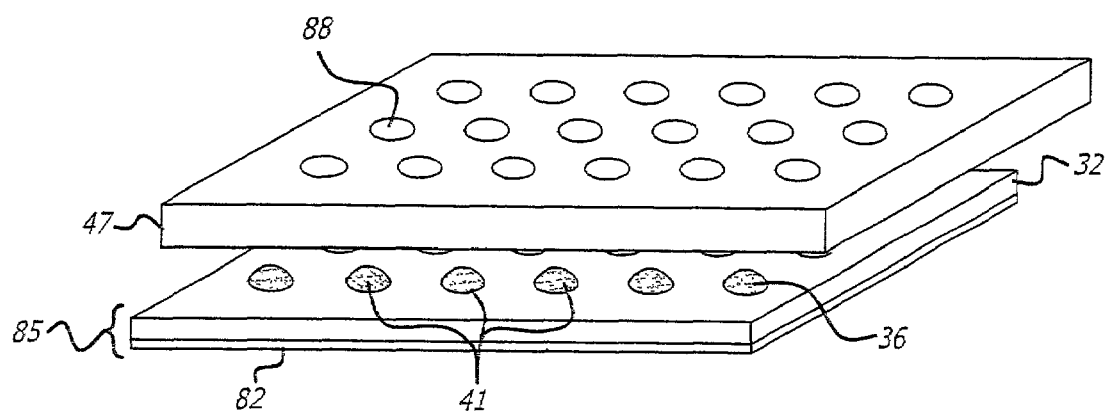
FIG. 14 is an elevated view of a substrate having a vapor sensitive coating on one side and a plurality of sample coatings arranged in an array on the other side in accordance with the present invention.

Once the coating of the water vapor sensitive composition 82 on substrate 32 is dry, a plurality of material, such as coating material 36, for example, in an array 41 may be disposed onto the side of the substrate 32 that is not coated with water vapor sensitive composition 82 as seen in FIG. 14. Methods of depositing sample coating materials or films onto a substrate 32 as detailed in other portions of this specification are likewise applicable to the water vapor sensor 85 which is comprised of substrate 32 and water vapor sensitive composition 82 coated thereon. An apertured template top 47 with a plurality of sample receiving receptacles 88 may be placed in engagement with substrate 32 in order to form material receiving wells, forming an array 41 of coating samples. The distance between sample coatings in the array 41, may be arranged to match the geometry of industry standard well plates so as to utilize various well plate reading/measuring devices.

Figure 15:
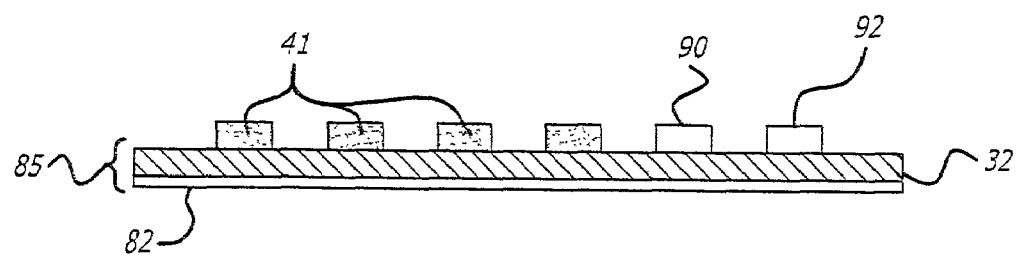
FIG. 15 is cross sectional view of a substrate with an array of coating material thereon disposed on one side of the substrate with the vapor sensitive material/composition on the other. Also shown are cross sections of optional reference or calibration areas.

FIG. 15 is an exemplary illustration of a cross sectional view of a substrate 32 with an array of coating material 41 thereon disposed on one side of the substrate 32 with the vapor sensitive composition 82 on the other. Also shown are cross sections of optional reference or calibration areas upon the substrate 32. At these positions, reference samples 90 and 92, such as glass or a piece of film may be disposed, utilizing adhesive, so as to calibrate the vapor sensor 85. The references may be highly impermeable to the vapor of interest, here water vapor, or may have some known permeability. For example, glass may be utilized as a highly impermeable reference. Similarly, a piece of film or a coating of known permeability having about 10-0.01 g $H_2O/m^2$-day, for example may be utilized as a calibration point or reference, to which the other material samples in the array 41 may be compared. Once calibrated, the vapor sensor 85 may be used as a measure to which other vapor sensors 85 having arrays 41 of coating materials having samples, thereon disposed, may be compared.

Once the water vapor sensor 85, as illustrated in FIG. 15, has the array of material 41 placed upon one side of substrate 32 and vapor sensitive composition 82 on the other, initial absorbance measurements are taken at each location having a sample of the array 41 and the calibration points, 90 and 92, if necessary, on the substrate 32. It should be noted that in the exemplary configuration detailed herein, the substrate is comprised of PET film. Thus, substrate 32 is flexible and in order to facilitate ease of handling, the water vapor sensor 85 with sample barrier coatings on one side and vapor sensitive composition 82 on the other, may be laminated, for example, to a plate of glass or other transparent backing material 96 having a high barrier to moisture.

Figure 16:
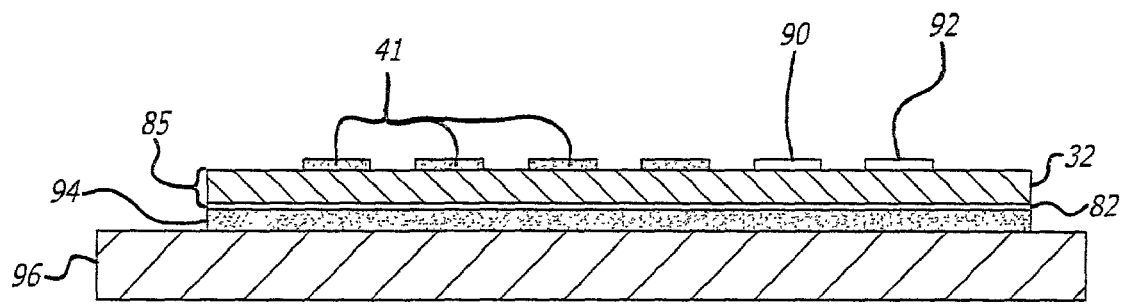
FIG. 16 is a cross sectional view of an exemplary multi-layered assembly utilized to test the vapor transmission rate or vapor barrier properties of a materials. In this depiction, the exemplary multi-layered assembly is mounted upon a support and anchored with a pressure sensitive adhesive.

Referring to FIG. 16, a cross sectional view of an exemplary multi-layered assembly utilized to test the vapor transmission rate or vapor barrier properties of an array sample coating materials 41 is shown. In this depiction, the water vapor sensor 85 is laminated to a high barrier transparent support 96 by a layer of pressure sensitive adhesive 94. This results in a stable unit 100 that may be transported as a whole, in order to perform various experimental steps, as detailed below.

Figure 17:
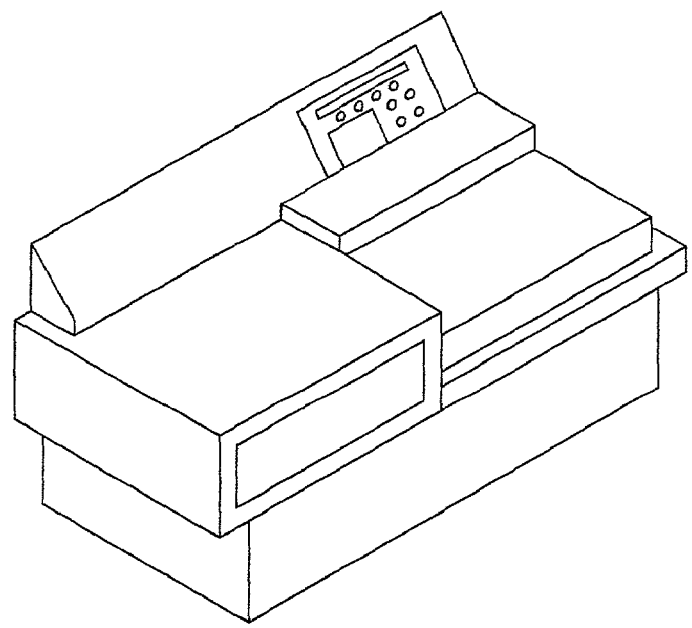
FIG. 17 is a perspective view of a commercially available well plate reader utilizable in an embodiment of the present invention.

Having arranged the coating samples in an advantageous array 41, the unit 100 is placed into a well plate reader, such as a Biotek μQuant, exemplified by FIG. 17. These measurement instruments are able to measure the absorbance of light at selected wavelengths of energy of a plurality of discrete locations. Therefore, the initial absorbance of each location upon the water vapor sensor 85 having a sample coating material 36 is recorded, as well as the calibration areas 90 and 91, if needed. Wavelengths utilized may range from about 400 to 800 nm, more preferably about 535, 580 and 630 nm. It is to be noted that the well plate reader is registering the absorbance of the entire thickness of the unit 100 at the locations where samples in the array 41 and references 90/91 are located.

After initial absorbances are noted for each sample location in the array 41, as well as the references 90 and 91, if calibration is necessary, the unit 100 in placed into a chamber containing the vapor of interest. The exemplary vapor of interest in this embodiment is water vapor, and accordingly, the unit is placed into a 100% humidity chamber.

As the water vapor permeates through the sample coatings in the array 41 and substrate 32, and reaches the coating of water vapor sensitive composition 82, the initially yellowish water vapor sensitive composition 82 begins to change color via the reaction detailed previously. The color change, beneath each sample location, of the water vapor sensitive composition 82 is correlated to the amount of water vapor that has permeated the sample coating 36 in the array 41 and substrate 32. With increasing amounts of water vapor penetrating through the sample coatings/films or barriers in the array 41 and substrate 32, the water vapor sensitive composition 82 underneath each sample location changes color from its initial yellowish coloration to a greenish tinge and then becomes bluish, or any range of colors in between. If water vapor sensitive composition 82 is exposed to a very high amount of water, the vapor sensitive composition 82 may become violet. It is this commensurate color change of the vapor sensitive composition 82 that is utilized to measure the moisture barrier properties of the sample coatings in the array 41.

At various times, the unit 100 is removed from the humidity chamber and the absorbancies of the various sample locations in the array 41, as well as the references 90 and 91, if calibration is necessary, are recorded and plotted onto a graph. The reference absorbancies over time provide a measure to which the barrier or vapor transmission properties of the sample coatings in an array 41 may be compared.

This graph typically plots the changing absorbance (color) of the water vapor sensitive composition 82 located underneath the coating samples of the array 41 and substrate 32. By plotting these absorbance changes, at the wavelengths previously mentioned, over time, the rate of transmission of the vapor through each of the sample coatings may be determined. This will be representative of the moisture barrier properties of the sample coatings to water vapor at 100% humidity.

It should be noted that in another exemplary configuration, the test formulations for coating materials or films may be coated directly on top of the water vapor sensitive composition 82. In this manner, the vapor of interest, here water vapor, that passes through the test formulations for coating materials or films does not then have to permeate the substrate 32 in order to interact with the water vapor sensitive composition 82. This provides for a more expedient method to determine vapor barrier characteristic of a coating material, for example. However, it may be noted that this configuration may not be optimal if the material to be tested in some way detrimentally modifies the water vapor sensitive composition 82.

While the well plate reader utilized in this particular embodiment measures the color change, or absorbance, of the water vapor sensitive composition 82 as an indication of the overlying coating material's 36 vapor barrier properties or vapor transmission rate, other measuring devices are further contemplated. For instance, if a device that measures color by reflectance is utilized, the backing 96 need not be transparent. As an example, backing 96 may be metallic. Additionally, if the sample coating material 36 is disposed directly upon a vapor sensitive composition 82 and color is measured by reflectance, the substrate 32 upon which the vapor sensitive composition 82 is coated need not be transparent.

Leveling Force

Once the different formulations are dispensed into a multi-well plate assembly 63, the coat formulations are made into flat coatings 64 within the wells by use of a leveling force. A "leveling force" as used herein, is defined as any force sufficient to cause a sample or coat material to distribute evenly and flatly onto a substrate. A leveling force will also remove any residual air bubbles present within the sample coat formulation. A variety of leveling forces are contemplated for use in the present invention including, for example, use of centrifugal force, use of a vacuum or negative pressure force, use of an electrostatic force, or use of a magnetic field. In the case where magnetic leveling force is used, the test coat formulation will contain magnetic particles, powder, or a compound such as ferrite, that is responsive to a magnetic force. Use of a leveling force need not be limited to single-coat assessments. Where the processing of a multi-layer construction of coat material is desired, a leveling force can be repeatedly applied following dispensing of individual layers of a coat to be tested. The final array obtained will be a planar sheet containing discrete areas in a grid format of multi-layer coat formulations.

Figure 11:
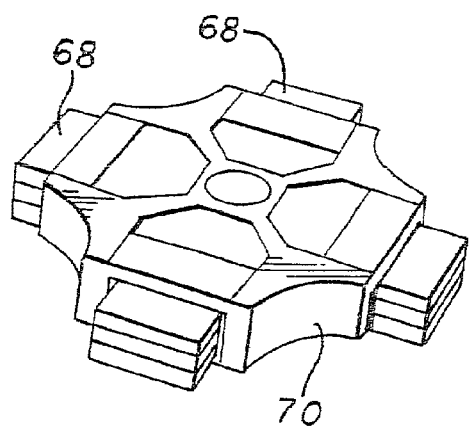
FIG. 11 is a perspective view of an example of a swing arm centrifuge rotor assembly usable in one embodiment of the invention, showing the assembly loaded with well plates.
Figure 12:
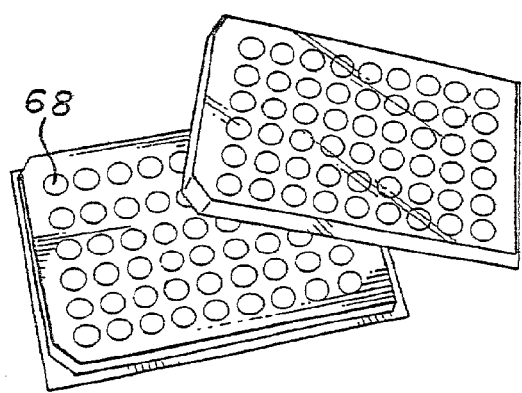
FIG. 12 is a perspective view of an example of a 96-well plate usable in one embodiment of the invention.

FIG. 11 shows an example of a centrifuge that can be used for applying a leveling force to a multi-well plate. Such swing arm-type centrifuges with multi-well plate holders (FIG. 12) are available commercially (for example, VWR Scientific, "MicroPlus GH 3.8 rotor centrifuge). The rotor for use in such a centrifuge is designed so as to hold an even number of multi-well plate assemblies. The multi-well plate assemblies 68 are loaded into the rotor 70 in an upright or horizontal position. During centrifugation, the plates are directed into a vertical position which then levels or flattens the sample formulations onto the substrate layer. After the formulations are dispensed in a multi-well plate assembly, the assembly is placed in a swing-arm centrifuge and the coatings are spun at controlled speeds so as to form a flat coating within each well 64. For example, with a standard centrifuge, a 10-min. spin at 2000 rpm will be sufficient to evenly distribute the coat materials within each well. There is no loss of sample material with use of a swing-arm centrifuge.

Figure 9:
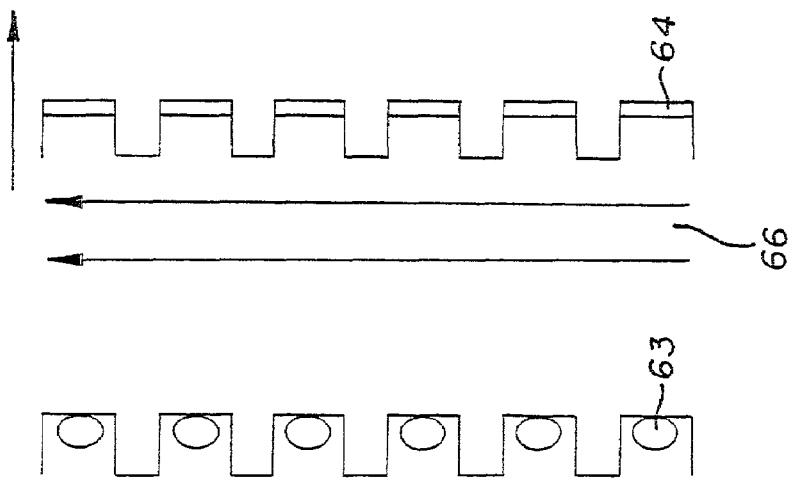
FIG. 9 is a schematic diagram showing leveling of coating array materials by application of a leveling force and curing by hot air.

Additional methods of casting sample coat formulations include those which can also simultaneously dry the coating material during casting. For example, a centrifuge which has been modified to hold circulating hot air or other gas which will aid in the evaporation of carrier solvents in the coating formulations is also contemplated for use in the present invention and is diagrammed schematically in FIG. 9. The hot air 66 circulating over the formulations during centrifugation aids in the drying of the coating by evaporation of volatiles or solvents. As with a centrifuge, devices used to provide alternative methods of applying a leveling force can also be modified so as to simultaneously dry the coat formulations. For example, an apparatus utilizing a vacuum or electrostatic force as the leveling force can be modified to circulate hot air and include alternate arrangements for drying.

High Throughput Analysis, Data Storage, Data Modeling and New Materials Discovery The above methods provide an array 40 of coating materials with each site in the grid array containing a coat material having a known parameter which differs from parameter values of the materials contained on the other sites (FIG. 1; step 16). With this array, the plurality of coating materials can each be tested for performance of each coating. Because the parameter value of the coating contained at each site is known, the value of a parameter associated with a desired performance of a coating can be determined. All information obtained by this high throughput analysis screening a coat material library are then entered into a database. From this database identification of the most successful new coat materials and the parameters and descriptors used to produce them is achieved (FIG. 1, step 23). Such a database will also serve as a storage library to aid in the formulation of future parameters to characterize the coatings.

EXAMPLE I

This example demonstrates the use of a multi-well plate combined with a centrifugal leveling force for estimation of coat weight of a sample coat material formulation. This example is intended to be representative of one embodiment of the invention, and not intended as limiting the scope of the invention.

The emulsion polymer formulation used was S-2000. S-2000 is a nondispersable emulsion acrylic polymer manufactured by Avery Dennison Corporation, Pasadena Calif. in accordance with U.S. Pat. No. 5,221,706. A 96-well plate obtained from Polytronics was used as a daughter well plate. The well plate remained flat during centrifugation. Each well contained an equivalent sample material formulation for determination of coat weight.

Diameter of each well=0.6 cm
Cross-section of each well=3.14×0.6 cm2=1.884 cm2
Weight of coat material in E7 position of array=0.0153 gm
Wet coat weight in E7=0.0153/0.0001884=81.21 gsm
% solids in wet solution=52.1%
Dry coat weight in E7=42.3 gsm
Results:

The emulsion did not dry fast and remained opaque. Hence the need for higher temperature drying. Material in wells located on the perimeter wells did not level evenly. Coat material dispensed into the center wells were centered and evenly flattened in the horizontal direction. The uneven leveling observed in the perimeter wells is believed to be a result of the centrifugal force acting at an angle to the bottom of the well, unlike the preferred flexible configuration of FIG. 6.

This example demonstrates the utility of using a multi-well plate combined with a leveling force for high-throughput analysis of specific parameters or characteristics of coat material formulations in an individualized manner.

The invention has been described with reference to various specific and preferred embodiments and techniques. However, it should be understood that many variations and modifications may be made while remaining within the spirit and scope of the invention. More specifically, for examples, (1) the apertured plate 47 could remain in place as part of the assembly of FIG. 16; (2) the array of samples to be tested may be retained in sample receptacles during testing, with the receptacles preferably having a known moisture permeability,; (3) as mentioned hereinabove, the samples may be deposited directly on the moisture sensitive layer 82; and (4) the array of samples to be tested may be formed by other techniques, and mounted in an array on the substrate or on the moisture sensitive layer. In addition, instead of making a series of measurements of color change, in some cases a single measurement of all samples may be made following a predetermined time interval of exposure to the vapor.

Accordingly, the present invention is not limited to the specific detailed description and showings set forth in the drawings.

We claim:

1. A high throughput method for determining vapor barrier characteristics of films and coatings comprising the steps of:
   preparing a vapor sensitive film;
   disposing a plurality of at least one of a coating and a film onto said vapor sensitive film;
   laminating said vapor sensitive film with said coatings and/or films onto a transparent backing;
   placing said transparent backing with said vapor sensitive film attached thereto and said coatings and/or films thereon disposed, into an absorbance measuring instrument;
   measuring an absorbance property of each of the coatings and/or films at spaced locations on said vapor sensitive film;
   placing said transparent backing with said vapor sensitive film attached thereto and said coatings and/or films thereon disposed, into a vapor chamber wherein a vapor of interest is present;
   removing said transparent backing with said vapor sensitive film attached thereto and said coatings and/or films thereon disposed from said vapor chamber at various times;
   placing said transparent backing with said vapor sensitive film attached thereto and said coatings and/or films thereon disposed, into said absorbance measuring instrument and measuring the absorbance of each of coatings and/or films locations on said vapor sensitive film again; and
   plotting the absorbance of said coatings and/or films locations versus time, in order to determine the barrier characteristics of said coatings.

2. The method of claim 1, wherein said plotting of said absorbance of said coatings and/or films locations versus time is utilized to determine a transmission rate of vapor through said coatings and/or films.

3. The method of claim 1, wherein areas of calibration are provided upon said vapor sensitive film.

4. The method of claim 1, wherein the preparation of said vapor sensitive film comprises the steps of: preparing a vapor sensitive composition comprising a predetermined amount of crystal-violet, perfluorosulfonate ion exchange polymer, alcohol and water;
   providing a substrate of film of predetermined size;
   coating a surface of said substrate of film with said vapor sensitive composition; and
   allowing the coating of said vapor sensitive composition disposed onto said substrate of film to dry.

5. The method of claim 1, wherein said absorbance measuring instrument is a well plate reader.

6. The method of claim 1, wherein said vapor of interest is water vapor.

7. A high throughput method for determining vapor barrier characteristics of films and coatings comprising the steps of:
   preparing a vapor sensitive film;
   disposing a plurality of at least one of a coating and/or a film onto said vapor sensitive film;
   laminating said vapor sensitive film with said coatings and/or films onto a transparent backing;
   placing said transparent backing with said vapor sensitive film attached thereto and said coatings and/or films thereon disposed, into an absorbance measuring instrument;
   measuring an absorbance property of each of the coatings and/or films at spaced locations on said vapor sensitive film;
   placing said transparent backing with said vapor sensitive film attached thereto and said coatings and/or films thereon disposed, into a vapor chamber wherein a vapor of interest is present;
   removing said transparent backing with said vapor sensitive film attached thereto and said coatings and/or films thereon disposed from said vapor chamber at various times;
   placing said transparent backing with said vapor sensitive film attached thereto and said coatings and/or films thereon disposed, into said absorbance measuring instrument and measuring the absorbance of each of coatings and/or films locations on said vapor sensitive film again; and
   plotting the absorbance of said coatings and/or films locations versus time, in order to determine the barrier characteristics of said coatings wherein the deposition of said plurality of coatings and/or films onto said vapor sensitive film comprises the steps of:
   providing a vapor sensitive film;
   utilizing said film as a substrate to form an array of sample receiving wells by overlying an apertured template top over said substrate, with said apertured template top in tight sealing engagement with said substrate;
   applying different samples of material in liquid form into said receiving wells;
   placing said substrate with said sample receiving wells containing said samples of material in liquid form thereon in a centrifuge;
   activating said centrifuge with said sample receiving wells mounted therein to flatten out the sample material in said sample receiving wells, with the centrifugal force acting perpendicular to the bottom of the sample receiving wells;
   drying or curing said samples while they are within the centrifuge; and removing the apertured template to leave said samples exposed on said substrate.

8. A high throughput method for determining vapor barrier characteristics of films and coatings comprising the steps of:
   preparing a vapor sensitive film;
   disposing an array of coatings and/or films in overlying relationship to said vapor sensitive film;
   laminating said vapor sensitive film with said coatings and/or films onto a transparent backing;
   placing said transparent backing with said vapor sensitive film attached thereto and said coatings and/or films thereon disposed, into an absorbance measuring instrument;
   measuring the absorbance of each of the coatings and/or films at spaced locations on said vapor sensitive film;
   exposing said transparent backing with said vapor sensitive film attached thereto and said coatings and/or films thereon disposed to the vapor of interest; and
   following a predetermined period of time of exposure to said vapor, placing said transparent backing with said vapor sensitive film attached thereto and said coatings and/or films thereon disposed, into an absorbance measuring instrument and measuring the absorbance of each of coatings and/or films of said array at spaced locations on said vapor sensitive film.

9. The method of claim 8 wherein areas of calibration are provided upon said vapor sensitive film.

10. A high throughput method for determining vapor barrier characteristics of films and coatings comprising the steps of:
preparing a vapor sensitive film;
disposing an array of coatings and/or films in overlying relationship to said vapor sensitive film;
laminating said vapor sensitive film with said coatings and/or films onto a transparent backing;
placing said transparent backing with said vapor sensitive film attached thereto and said coatings and/or films thereon disposed, into an absorbance measuring instrument;
measuring the absorbance of each of the coatings and/or films at spaced locations on said vapor sensitive film;
exposing said transparent backing with said vapor sensitive film attached thereto and said coatings and/or films thereon disposed to the vapor of interest; and
following a predetermined period of time of exposure to said vapor, placing said transparent backing with said vapor sensitive film attached thereto and said coatings and/or films thereon disposed, into an absorbance measuring instrument and measuring the absorbance of each of coatings and/or films of said array at spaced locations on said vapor sensitive film;
wherein the deposition of said array of coatings and/or films onto said vapor sensitive film comprises the steps of:
providing a vapor sensitive film;
utilizing said film as a substrate to form an array of sample receiving wells by overlying an apertured template top over said substrate, with said apertured template top in tight sealing engagement with said substrate;
applying different samples of material in liquid form into said receiving wells; placing said substrate with said sample receiving wells containing said samples of material in liquid form thereon in a centrifuge;
activating said centrifuge with said sample receiving wells mounted therein to flatten out the sample material in said sample receiving wells, with the centrifugal force acting perpendicular to the bottom of the sample receiving wells;
drying said samples while they are within the centrifuge; and
removing the apertured template to leave said samples exposed on said substrate.

11. A method for determining vapor barrier characteristics of films and coatings comprising the steps of:
preparing a vapor sensitive film;
disposing a coating or film to be tested in overlying relationship to said vapor sensitive film;
laminating said vapor sensitive film and said coating or film onto a substrate;
exposing said substrate with said vapor sensitive film, and said coating or film disposed thereon, to the vapor of interest; and
following a predetermined period of time of exposure to said vapor, placing said substrate with said vapor sensitive film attached thereto and said coating or film disposed thereon, into an optical measuring instrument and measuring an optical property of said vapor sensitive film.

12. The method for determining vapor barrier characteristics of films and coatings of claim 11, wherein said optical measuring instrument measures absorbance.

13. The method for determining vapor barrier characteristics of films and coatings of claim 11, wherein said vapor sensitive film is comprised of a light absorbing organic dye or organic dye composition.

14. The method for determining vapor barrier characteristics of films and coatings of claim 13, wherein said organic dye or organic dye composition is comprised of crystal violet and perfluorosulfonate ion exchange polymer.

* * * * *